United States Patent
Evans et al.

(10) Patent No.: US 7,745,113 B2
(45) Date of Patent: Jun. 29, 2010

(54) USE OF ISLET 1 AS A MARKER FOR ISOLATING OR GENERATING STEM CELLS

(75) Inventors: Sylvia M. Evans, Del Mar, CA (US); Ju Chen, San Diego, CA (US); Chenleng Cai, San Diego, CA (US); Alessandra Moretti, La Jolla, CA (US); Kenneth R. Chien, La Jolla, CA (US); Karl-Ludwig Laugwitz, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 284 days.

(21) Appl. No.: 10/544,053

(22) PCT Filed: Feb. 2, 2004

(86) PCT No.: PCT/US2004/002978

§ 371 (c)(1),
(2), (4) Date: Apr. 13, 2006

(87) PCT Pub. No.: WO2004/070013

PCT Pub. Date: Aug. 19, 2004

(65) Prior Publication Data

US 2006/0246446 A1    Nov. 2, 2006

Related U.S. Application Data

(60) Provisional application No. 60/444,247, filed on Jan. 31, 2003, provisional application No. 60/484,809, filed on Jul. 2, 2003.

(51) Int. Cl.
*C12Q 1/68* (2006.01)
*G01N 33/567* (2006.01)
*C12N 5/71* (2006.01)
(52) U.S. Cl. .............................. 435/6; 435/366; 435/7.2
(58) Field of Classification Search ........................ None
See application file for complete search history.

(56) References Cited

FOREIGN PATENT DOCUMENTS

WO    WO 02/12498    2/2002

OTHER PUBLICATIONS

Amit et al (Developmental Biology. 2000.227: 271-278).*
Ericson (Science. Jun. 12, 1992; col. 256: 1555-1560).*
Hamburger et al. (J. Morphol. 1951; 88: 49-92).*
Encyclopaedia Brittanica—somite definition.*
Edinburgh Mouse Atlas.*
ISSCR—Glossary of Stem Cell Related Terms.*
Boyer et al. (Cell. 2005; 122: 947-956).*
Boheler et al. (Circulation Research. 2002; 91: 189-201).*
Pfaff et al. (Cell 1996; 84:309-320).*
Schilling et al. (Developmental Biology 1999. 210: 277-287).*
Yuan et al. (The Anatomical Record. 2000; 260:204-207).*
Ahlgren et al., "Independent Requirement for ISL1 in Formation of Pancreatic Mesenchyme and Islet Cells." *Nature* 385(6613):257-260 (1997).
Cai et al., "Isl1 Identifies a Cardiac Progenitor Population that Proliferates Prior to Differentiation and Contributes a Majority of Cells to the Hart." *Developmental Cell* 5:877-889 (2003).
Pfaff et al., "Requirement for LIM Homeobox Gene *Isl1* in Motor Neuron Generation Reveals a Motor Neuron-Dependent Step in Interneuron Differentiation." *Cell* 84:309-320 (1996).
Stenman et al., "Identification of Two Distinct Progenitor Populations in the Lateral Ganglionic Eminence: Implications for Striatal and Olfactory Bulb Neurogenesis." *The Journal of Neuroscience* 23(1):167-174 (2003).

* cited by examiner

*Primary Examiner*—Scott Long
(74) *Attorney, Agent, or Firm*—DLA Piper LLP (US)

(57) ABSTRACT

The present invention provides in vitro methods of expansion and propagation of undifferentiated progenitor cells and more specifically undifferentiated progenitor cells containing Islet1, a marker apparently unique to proliferating cardiac stem cells. Methods are described for isolation of stem cell populations as well as for provoking expansion and propagation of undifferentiated progenitor cells without differentiation, to provide cardiac repair or improve cardiac function, for example.

15 Claims, 2 Drawing Sheets

SEQ ID NO:1 mRNA sequence of EST of Islet 1

GGTCCCGAGCCGTGCAGGTCCGCCGCTGCTGCTGCGCCTCCGCTCTGCCAACTCCGCCGG

CTTAAATCGGACTCCCAGATCTGCGAGGGCGCGGCGCAGCCAGNCGTGTTTCCCCCAGTT

TTGGCAACCCCGGGGGCCACTATTTGCCACCTAGCCACAGCACCAGCATCCTCTCTGTGG

GCTATTCACCAATTGTCCAACCACCATTTCACTGTGGACATTACTCCCTCTTACAGATAT

GGGAGACATGGGCGATCCACCAAAAAAAAAACGTCTGATTTCCCTGTGTGTTGGTTGCGG

CAATCAAATTCACGACCAGTATATTCTGAGGGTTTCTCCGGATTTGGAGTGGCATGCAGC

ATGTTTGAAATGTGCGGAGTGTAATCAGTATTTGGACGAAAGCTGTACGTGCTTTGTTAG

GGATGGGAAAACCTACTGTAAAGAGATTATATCAGGTTGTACGGGATCAAATGCGCCAA

GTGCAGCATAGGCTTCAGCAAGAACGACTTCGTGATGCGTGCCCGCTCTAAGGTGTACCA

CATCGAGTGTTTCCGCTGTGTAGCCTGCAGCCGACAGCTCATCCCGGGAGACGAATTCGC

CCTGGCGGAGGATGGGCTTTTCTGCCGTGCGANCCACGATGTGTNGGAGAGAGCCAGGCT
GGGAGCTGGAGACCCTCTCAGTCCCTTGCATCCAGCGCGC

FIG. 1

SEQ ID NO:2   AMINO ACID SEQUENCE OF ISLET1 (Mouse)

MGDMGDPPKKKRLISLCVGCGNQIHDQYILRVSPDLEWHAACLK

CAECNQYLDESCTCLVRDGKTYCKRDYIRLYGIKCAKCSIGFSKNDFVMRARSKVYHI

ECFRCVACSRQLIPGDEFALREDGLFCRADHDVVERASLGAGDPLSPLHPARPLQMAA

EPISARQPALRPHVHKQPEKTTRVRTVLNEKQLHTLRTWYAANPRPDALMKEQLVEMT

GLSPRVIRVWFQNKRCKDKKRSIMMKQLQQQQPNDKTNIQGMTGTPMVAASPERHDGG

LQANPVEVQSYQPPWKVLSDFALQSDIDQPAFQQLVNFSEGGPGSNSTGSEVASMSSQ
LPDTPNSMVASPIEA

FIG. 2

SEQUENCE LISTING

<160> NUMBER OF SEQ ID NOS: 2

<210> SEQ ID NO 1
<211> LENGTH: 700
<212> TYPE: DNA
<213> ORGANISM: Mouse
<220> FEATURE:
<221> NAME/KEY: misc_feature
<222> LOCATION: (1)..(700)
<223> OTHER INFORMATION: n is any nucleotide

<400> SEQUENCE: 1

```
ggtcccgagc cgtgcaggtc cgccgctgct gctgcgcctc cgctctgcca actccgccgg      60
cttaaatcgg actcccagat ctgcgagggc gcggcgcagc cagncgtgtt tcccccagtt     120
ttggcaaccc cggggccac  tatttgccac ctagccacag caccagcatc ctctctgtgg     180
gctattcacc aattgtccaa ccaccatttc actgtggaca ttactccctc ttacagatat     240
gggagacatg ggcgatccac caaaaaaaaa acgtctgatt tccctgtgtg ttggttgcgg     300
caatcaaatt cacgaccagt atattctgag ggtttctccg gatttggagt ggcatgcagc     360
atgtttgaaa tgtgcggagt gtaatcagta tttggacgaa agctgtacgt gctttgttag     420
ggatgggaaa acctactgta aaagagatta tatcaggttg tacgggatca aatgcgccaa     480
gtgcagcata ggcttcagca agaacgactt cgtgatgcgt gcccgctcta aggtgtacca     540
catcgagtgt ttccgctgtg tagcctgcag ccgacagctc atcccgggag acgaattcgc     600
cctggcggag gatgggcttt tctgccgtgc ganccacgat gtgtnggaga gagccaggct     660
gggagctgga gaccctctca gtcccttgca tccagcgcgc                           700
```

<210> SEQ ID NO 2
<211> LENGTH: 349
<212> TYPE: PRT
<213> ORGANISM: Mouse

<400> SEQUENCE: 2

```
Met Gly Asp Met Gly Asp Pro Lys Lys Lys Arg Leu Ile Ser Leu
1               5                   10                  15

Cys Val Gly Cys Gly Asn Gln Ile His Asp Gln Tyr Ile Leu Arg Val
            20                  25                  30

Ser Pro Asp Leu Glu Trp His Ala Ala Cys Leu Lys Cys Ala Glu Cys
        35                  40                  45

Asn Gln Tyr Leu Asp Glu Ser Cys Thr Cys Leu Val Arg Asp Gly Lys
    50                  55                  60

Thr Tyr Cys Lys Arg Asp Tyr Ile Arg Leu Tyr Gly Ile Lys Cys Ala
65                  70                  75                  80

Lys Cys Ser Ile Gly Phe Ser Lys Asn Asp Phe Val Met Arg Ala Arg
                85                  90                  95

Ser Lys Val Tyr His Ile Glu Cys Phe Arg Cys Val Ala Cys Ser Arg
            100                 105                 110

Gln Leu Ile Pro Gly Asp Glu Phe Ala Leu Arg Glu Asp Gly Leu Phe
        115                 120                 125

Cys Arg Ala Asp His Asp Val Val Glu Arg Ala Ser Leu Gly Ala Gly
    130                 135                 140

Asp Pro Leu Ser Pro Leu His Pro Ala Arg Pro Leu Gln Met Ala Ala
145                 150                 155                 160

Glu Pro Ile Ser Ala Arg Gln Pro Ala Leu Arg Pro His Val His Lys
```

-continued

```
                165                 170                 175
Gln Pro Glu Lys Thr Thr Arg Val Arg Thr Val Leu Asn Glu Lys Gln
            180                 185                 190
Leu His Thr Leu Arg Thr Trp Tyr Ala Ala Asn Pro Arg Pro Asp Ala
            195                 200                 205
Leu Met Lys Glu Gln Leu Val Glu Met Thr Gly Leu Ser Pro Arg Val
            210                 215                 220
Ile Arg Val Trp Phe Gln Asn Lys Arg Cys Lys Asp Lys Lys Arg Ser
225                 230                 235                 240
Ile Met Met Lys Gln Leu Gln Gln Gln Pro Asn Asp Lys Thr Asn
            245                 250                 255
Ile Gln Gly Met Thr Gly Thr Pro Met Val Ala Ala Ser Pro Glu Arg
            260                 265                 270
His Asp Gly Gly Leu Gln Ala Asn Pro Val Glu Val Gln Ser Tyr Gln
            275                 280                 285
Pro Pro Trp Lys Val Leu Ser Asp Phe Ala Leu Gln Ser Asp Ile Asp
    290                 295                 300
Gln Pro Ala Phe Gln Gln Leu Val Asn Phe Ser Glu Gly Gly Pro Gly
305                 310                 315                 320
Ser Asn Ser Thr Gly Ser Glu Val Ala Ser Met Ser Ser Gln Leu Pro
            325                 330                 335
Asp Thr Pro Asn Ser Met Val Ala Ser Pro Ile Glu Ala
            340                 345
```

USE OF ISLET 1 AS A MARKER FOR ISOLATING OR GENERATING STEM CELLS

CROSS REFERENCE TO RELATED APPLICATIONS

This application is a 35 USC §371 National Stage application of PCT Application No. PCT/US2004/002978 filed Feb. 2, 2004; which claims the benefit under 35 USC §119(e) to U.S. Application Ser. No. 60/444,247 filed Jan. 31, 2003, and U.S. Application Ser. No. 60/484,809 filed Jul. 2, 2003. The disclosure of each of the prior applications is considered part of and is incorporated by reference in the disclosure of this application.

GRANT INFORMATION

This invention was made with government support under Grant No. HL66276 awarded by the National Institutes of Health. The United States government has certain rights in this invention.

FIELD OF THE INVENTION

The invention relates generally to in vitro expansion and propagation of undifferentiated progenitor cells and more specifically to undifferentiated progenitor cells containing Islet1.

BACKGROUND INFORMATION

Congenital heart disease is the most common of all birth defects (Hoffman and Kaplan, 2002). For successful prevention of or therapeutic intervention in congenital heart disease, it is of utmost importance to understand its etiology. Toward this goal, an understanding of the origin of specific cardiac lineages and their interactions with each other is critical. Understanding the origin and properties of cardiac progenitors is also important for the development of cardiac stem cell therapies for both congenital and adult heart disease.

Recent work has defined two fields of cardiac progenitors, dubbed the primary and secondary, or anterior heart fields (Kelly and Buckingham, 2002). The primary heart field is believed to give rise to the atria and ventricles of the heart, while the secondary or anterior field is believed to give rise to the outflow tract. The secondary field is believed to reside anterior and dorsal to the heart at the early linear heart tube stage. Initial evidence that the outflow tract of the heart was not present in the linear heart tube came from a series of in vivo lineage studies performed in chick embryos by de la Cruz and colleagues from 1977 onward (de la Cruz, 2000). These studies demonstrated that the outflow tract was not present at the linear heart tube stage, but did not indicate where the outflow tract came from at a later stage.

Recently, the source of the outflow tract has been addressed by studies from three different laboratories, two performed in chick embryos, and one performed in mouse embryos (Kelly et al., 2001; Mjaatvedt et al., 2001; Waldo et al., 2001). Results of these studies demonstrated that some cells in the outflow tract originate from splanchnic mesoderm adjacent to the pharyngeal endoderm. The extent of the contribution, and the boundaries of the "secondary" or "anterior" heart field could not be definitively assessed from results of these experiments.

Stem cells have been defined in many different ways. However, the main principles include: (1) self-renewal, or the ability to generate daughter cells with characteristics similar to the initiating mother cell; (2) multi-lineage differentiation of a single cell; and (3) in vivo functional reconstitution of damaged tissue.

The Embryonic Stem (ES) cells, first obtained from mouse (Evans and Kaufmann, 1981) and more recently from non-human primates and human blastocysts (Thomson, et al., 1998), display all three characteristics. ES cells are pluripotent cells derived from the inner cell mass of the blastocyst that can be propagated indefinitely in an undifferentiated state. Both mouse and human ES cell-lines have been maintained continuously in culture for more than 300 cell doublings. ES cells differentiate into all somatic cell types when injected into a blastocyst and form mature progeny cells of all three embryonic germ layers in vitro. Finally, all differentiated progeny of ES cells are functional cells, as mice generated by tetraploid embryo complementation are viable. Although ES cells have been isolated from humans, their use in research as well as their therapeutic potential is encumbered by ethical considerations.

Most adult stem cells also fulfil the stem cell criteria mentioned above, even though the degree of self-renewal and differentiation is less than that seen for ES cells. The best studied adult stem cell, the hematopoietic stem cell (HSC) (Weissman, 2000), undergoes in vivo self-renewing cell divisions, differentiates at the single cell level into all mature blood elements, and functionally repopulates the bone marrow of myeloablated animals and humans. Other adult stem cells have been more recently defined and are, therefore, less well studied. However, neural stem cells (NSC) (Gage, 2000), mesenchymal stem cells (MSC) (Jiang, et al., 2002) and epidermal stem cells (Toma, et al., (2001) all fulfil these basic criteria. Other cells also termed stem cells, such as angioblasts or endothelial stem cells (Rafii, et al., 1994), display all the required characteristics, except that they differentiate only into a single type of cells.

Over the last few years a plethora of literature has been published indicating that cells from a given tissue might be capable of differentiating into cells of a different tissue "Stem cell plasticity" is a new term that has been used to describe the recent observations that greater potential might persist in postnatal adult stem cells than previously expected. The majority of studies using bone marrow (BM), or peripheral blood enriched for HSC were based on in vivo transplantation of either sex-mismatched cells or genetically marked cells, and detection of donor cells was based on the presence of the Y-chromosome or the marker gene. There are excellent reviews of the pitfalls involved in the detection of donor cells using either marking system (Tisdale and Dunbar, 2002). Differentiation, not only into hematopoietic cells, but also into cells with characteristics of skeletal muscle (Gussoni, et al., 1999), cardiac muscle (Orlic, et al., 2001), endothelium (Jackson, et al., 2001), neuroectoderm (Brazelton, et al., 2000) and endodermal cells (Krause, et al., 2001), including hepatocytes, has been described.

In 80% of these studies, fresh BM cells were transplanted without prior in vitro culture, so that the question of whether the cell with plasticity can undergo self-renewal could not be assessed. In the majority of these studies, non-purified populations of cells or cells purified to partial homogeneity were transplanted, therefore making it impossible to study the clonal origin of differentiated cells or the tissue of origin of cells with characteristics of a second tissue. Finally, these studies depended on phenotypic characteristics to define differentiation into cells different from the tissue of origin, but have yet to demonstrate that the cells of the second tissue have functional characteristics of that lineage.

Thus there is need in the art for new and better methods of in vitro expansion and propagation of undifferentiated cardiac progenitor cells. The method includes culturing isolated undifferentiated progenitor cells that express Islet1 under conditions sufficient for progenitor cell growth. study of

SUMMARY OF THE INVENTION

Analysis of mice lacking Islet1, a LIM homeodomain transcription factor, has revealed a new paradigm for heart development. Hearts of islet1 knockout mice are completely missing the outflow tract, right ventricle, and much of the atria. Islet1 expression and lineage tracing of islet1-expressing progenitors demonstrate that Islet1 is a marker for a distinct population of undifferentiated cardiac progenitors that give rise to cardiac segments found missing in isl 1 mutants. Islet1 function is required for these progenitors to contribute to the heart. In islet1 mutants, islet1 expressing progenitors are progressively reduced in number, and bone morphogenetic proteins (BMPs), and fibroblast growth factors (FGFs) are down regulated. The studies described herein define two cardiogenic fields, of which one expresses and requires Islet and the other does not. The results of these studies have implications for the development of specific cardiac lineages, cardiac looping, left right asymmetry, cardiac evolution, and cardiac stem cells.

Accordingly, in one embodiment, the invention provides a method for detecting a stem cell comprising determining expression of Islet1 nucleic acid or expression product in a cell.

In another embodiment, the invention provides a method for isolating or enriching for stem cells comprising contacting the cells with an agent reactive with Islet1 and separating the reactive positive cells from reactive negative cells, thereby isolating or enriching for stem cells.

In yet another embodiment, the invention provides methods for generating a stem cell comprising contacting an undifferentiated progenitor cell that expresses Islet 1 with an agent that activates or enhances expression of Islet1 in the cell so as to activate or enhance expression of Islet 1 in the cell.

In still another embodiment, the invention provides an in vitro method for expansion and propagation of undifferentiated cardiac progenitor cells. The method includes culturing isolated undifferentiated progenitor cells that express Islet1 under conditions sufficient for progenitor cell growth. In the method, the conditions sufficient for progenitor cell growth include culturing the cells on a feeder layer of species-specific cardiac fibroblasts or conditioned medium of fibroblasts from the heart.

In another embodiment, the invention provides a composition that is an enriched population of Islet1 positive stem cells comprising greater than 90% Islet1 positive stem cells, as compared with other cell types.

BRIEF DESCRIPTION OF THE DRAWINGS

FIG. 1 is the mRNA sequence of an EST of Islet 1 (SEQ ID NO:1).

FIG. 2 is the DNA sequence of Islet 1 (mouse) available through GenBank under accession number: NM_021459 XM_354773. (SEQ ID NO:2).

DETAILED DESCRIPTION OF THE INVENTION

It has been discovered that Islet1 (SEQ ID NO: 2) is a transcription factor that is a unique marker for proliferating cardiac stem cells (FIG. 2). It is the only gene known to date that is specifically expressed in cardiogenic stem cells, but not in differentiated cardiac cells. Islet1 may be a master regulator of the cardiogenic stem cell state. This discovery enables use of islet1 expression as a means to isolate endogenous cardiogenic stem cells, or to create cardiogenic stem cells. Islet1 is also expressed in other progenitor, or "stem cell" populations, including those of the pancreas, the neural crest, the aorta-gonad-mesonephros region (hematopoietic and endothelial progenitors), and other cell types. This expression, in concert with data described herein pertaining to cardiogenic stem cells, shows that islet marks, not only cardiogenic stem cells, but other pluripotent stem cells as well.

No other gene is known that is specifically expressed in undifferentiated cardiogenic precursors at earliest stages. Islet1 is a unique identifier of this cell population. Islet1 is also required for these precursors to contribute to development of the heart. In islet1 mutants, cardiogenic lineages normally derived from islet1-expressing progenitors are absent. Thus, Islet is unique in being expressed in a number of embryonically distinct pluripotential progenitors. Islet is a transcription factor that drives the stem cell state.

Utilizing islet1 as a marker, cells can be isolated from early embryos, hybridized with fluorescently labelled islet1 antibodies, and sorted for stem cells by FACS. Alternatively, genes (eg. lacZ, GFP, cre) can be inserted into the endogenous islet1 locus and used as a basis of cell identification or sorting. Cardiogenic stem cell lines can be created by expressing islet1 alone or in combination with Nkx2.5, another transcription factor that is expressed in cardiac progenitors, but is also expressed in differentiated cardiac cells. To differentiate these cardiogenic precursors, islet1 expression was down-regulated by genetic means or by application of growth factors. Other stem cell lines can be created in a similar manner, expressing islet1 alone or in combination with other factors specific to distinct lineages, to create pluripotent cells, which can differentiate to multiple lineages, or specific lineages dependent on the genetic or physical environment.

A large body of data attests to the conclusion that islet1 is a marker of cardiogenic stem cells prior to their differentiation. This finding has led to the concept of utilizing islet1 as a means to isolate cardiogenic stem cells, from embryonic, neonatal or adult stages from a variety of experimental model animals, and from humans. An islet1 antibody can be obtained to detect these cell populations, and a mouse line in which GFP has been inserted into the islet1 locus, using known techniques, can be created. It has also been determined that islet is expressed in the aorta-gonad-mesonephros region, a region critical for generating multipotential hematopoietic and endothelial precursors.

Several therapeutic applications arise from the studies described herein utilizing these stem cells. For example, methods are provided for converting distinct cell types into cardiogenic stem cells for therapeutic application: e.g., isolation of skin fibroblasts or bone marrow stem cells from a cardiac patient, converting these cells to cardiogenic cells, and then injecting the converted cells into the patient. This method can be used to treat cardiac diseases, including post-infarct, heart failure, ischemic heart disease. Other applications include provoking proliferation and/or differentiation of resident cardiogenic stem cells within the differentiated heart to provide cardiac repair or improve cardiac function. Isolated cardiogenic stem cells can be used for therapeutic drug screening, for toxicology studies and for tissue engineering. In all of these procedures, other distinct cell lineages that may be derived from islet positive stem cells can also be used, with applications to relevant human disease.

The invention is based on the discovery that boundaries of the two cardiogenic fields are different than previously expected. One progenitor population expresses islet1 and will give rise to the outflow tract, right ventricle, a subset of left ventricular cells, and a majority of atrial cells. The other does not express islet1, and will give rise to a subset of the left ventricular cells and some atrial cells. The specific expression of islet1 in undifferentiated precursors also allows, for the first time, a precise visualization of the islet1 expressing progenitor population, and gives us an important handle for the isolation and characterization of a cardiac stem cell population. Islet1 not only defines this stem cell population, but is also required for these cells to contribute to the heart, providing the first genetic evidence for distinct heart fields.

Islet1 (Isl 1) knockout mice have been examined for defects in both motor neuron and pancreatic development (Ahlgren et al., 1997; Pfaff et al., 1996). Mice which are homozygous null for isl 1 exhibit growth retardation at approximately ED9.5, and die at approximately ED10.5. Heterozygous mutants survive, and have no apparent phenotype. The cause of death in homozygous mutants has not previously been addressed, although vascular abnormalities were suspected (Pfaff et al., 1996). Therefore the cause of death in isl $1^{-/-}$ mice was examined.

When homozygous null embryos between ED9.0 to ED9.5 were examined, severely abnormal hearts were found. At a gross morphological level, mutant hearts appeared to consist of a single, misshapen, and undivided chamber. Histological analysis confirmed this impression. As an initial attempt to characterize chamber identity of cells within mutant hearts, whole mount in situ hybridization analysis with markers for cardiac chambers was performed. Ventricular myosin light chain 2 (MLC2v) mRNA specifically marks ventricular cells, and cells of the A/V junction (Franco et al., 1999). At these stages, atrial myosin light chain 2 (MLC2a) mRNA marks all myocardial cells (Kubalak et al., 1994). Hybridization with probes for MLC2v and MLC2a mRNAs demonstrated that cells within the anterior part of the single chamber had ventricular identity, whereas cells in the posterior part of the single chamber did not, and were therefore likely to have atrial identity.

A number of transcription factors are regionally expressed within the heart, and a panel of these was used to further explore cellular identity within isl 1 mutant hearts. At stages examined, tbx5 is specifically expressed in the posterior pole of the heart, in atria and left ventricle (Bruneau et al., 1999). In islet1 mutants, both atrial and ventricular segments of the heart expressed tbx5, indicating that ventricular portions of the mutant heart had left ventricular identity. EHand is expressed in left ventricle, but not right ventricle (Cross et al., 1995; Cserjesi et al., 1995; Thomas et al., 1998). In isl $1^{-/-}$ embryos, EHand was expressed throughout the ventricular tissue, indicating that it had left ventricular identity, not right ventricular identity, consistent with results obtained with the tbx5 probe. Tbx20 is highly expressed in the outflow tract and in the A/V canal (Carson et al., 2000; Kraus et al., 2001). Hearts from islet1 mutants expressed tbx20 at the junction of the ventricle and atria, but did not express tbx20 at their anterior end, indicating an absence of the outflow tract. Results consistent with this were obtained with a probe for msx2, which marks the outflow tract of the heart at ED8.5. Islet1 mutant hearts had no anterior staining of msx2. Together with the previous results from hybridization with probes for MLC2a and MLC2v, these data indicated that islet1 mutants were lacking an outflow tract and right ventricle, although cells with left ventricular, A/V canal, and atrial identities were present.

From this analysis, it was inferred that islet1 mutants were missing complete segments of the heart. Additionally, mutant hearts had not undergone looping. This conclusion was strengthened by scanning electron microscopy analysis. Intriguingly, cardiac primordia in isl 1 mutants at ED 9.0 (12 somite pairs) resembled cardiac primordia seen in wild type embryos at earlier stages, at ED 8.25 (5 somite pairs) (Kaufman, 1999), indicating an interruption in heart development. A comparison of wild type littermates to their mutant counterparts at ED 9.5 (22 somite pairs) showed an absence of outflow tract and right ventricle in mutants, consistent with marker analysis.

The severe cardiac phenotype of isl $1^{-/-}$ mice led to investigation of expression of isl 1 during early stages of mouse heart development. Single and double whole mount in situ hybridization was performed on embryos from ED7.25 to ED 8.75, utilizing probes for isl 1 and MLC2a mRNAs. The latter is one of the earliest markers for differentiated cardiogenic precursors. Results of this whole mount in situ and subsequent section analysis demonstrated that islet1 is never co-expressed with MLC2a, but rather is expressed in an immediately adjacent population of cells. At the early cardiogenic crescent stages, islet1 expressing cells are medial and dorsal to MLC2a expressing cells. As the heart tube forms, islet1 positive cells within splanchnic mesenchyme comprising the mesocardium and adjacent to foregut endoderm are contiguous with MLC2a positive cells throughout their extent, including anterior and posterior regions. Islet1 is expressed in both splanchnic mesoderm and in ventral foregut endoderm.

Although islet1 was not expressed in differentiating MLC2a positive myocardial precursors, it was expressed in the region of the recently identified secondary or anterior heart field, that is, splanchnic mesodermal cells of the pharyngeal region. Recent evidence has indicated that the anterior heart field in mouse contributes to the outflow tract (Kelly and Buckingham, 2002). This observation, in concert with the cardiac phenotype in islet1 mutants, indicated that islet1 expressing cells might contribute to the outflow tract of the heart.

To investigate this question, lineage analysis of isl 1 expressing cells was performed, by crossing an islet1-cre mouse (Srinivas et al., 2001) with the Rosa26-lacZ indicator mouse (Soriano, 1999). In progeny of this cross, Cre-mediated excision brings the lacZ gene under the control of the ubiquitously expressed Rosa26 locus, enabling the fate of isl 1 expressing cells to be followed by staining for β-galactosidase activity, even when transcription from the endogenous isl 1 locus has been repressed. Results of this analysis were startling, and demonstrated that cells which previously expressed islet1 make a substantial contribution to the embryonic heart, comprising a majority of cells in the outflow tract, right ventricle, and atria, and also contribute to specific regions of the left ventricle. The β-galactosidase positive cells were also observed within the endocardium, and within endothelial cells lining the aortic arch arteries. The majority of β-galactosidase negative myocardial cells were observed within the ventral aspect of the left ventricle and the anterior ventral region of the left atria.

The observation that islet1-expressing cells contribute a majority of cells to the developing heart was consistent with our previous analysis of the cardiac phenotype in isl 1 homozygous mutant mice, where whole segments of the heart were missing. The missing structures indicated that Islet1 might be required for proliferation, survival and/or migration of islet1 expressing cardiogenic precursors. To address this question, an attempt was made to examine isl 1 expressing cells within isl 1 mutants and littermate controls. Although targeting of the isl 1 gene deleted the third exon, containing the second LIM domain, the 5' end of isl 1 mRNA is still expressed in the mutant, enabling detection of islet1 message in mutant cells. Islet protein, however, is not detectable (Pfaff et al., 1996).

To track isl 1 expressing cells in mutant and wild type embryos, whole mount in situ hybridization analysis was performed on embryos from ED8.5-ED10 with a probe for isl 1 mRNA. Results of this analysis demonstrated that there are progressively fewer islet-expressing cells in the mutant, although some cells still remain. In conjunction with the cardiac phenotype of isl 1 mutants, these results indicate that Islet is required for cell proliferation and/or cell survival.

The results of these studies show that Islet1 is required cell for proliferation and survival of cardiogenic precursors, and that downstream targets of Islet1 are mediating this effect. Two growth factor pathways which have been implicated in growth and survival of cardiogenic precursors in both vertebrate and invertebrate heart development are bone morphogenetic proteins (BMPs), and fibroblast growth factors (FGFs) (Kirby, 2002; Yutzey and Kirby, 2002). A number of BMPs and FGFs have been described as being expressed in embryonic regions that overlap with and/or are adjacent to islet1-expressing cells, including BMPs 2, 4, 6 and 7, and FGFs 4, 8, and 10 (Crossley and Martin, 1995; Dudley and Robertson, 1997; Kelly et al., 2001; Lyons et al., 1995; Niswander and Martin, 1992). To determine if any of these are targets of Islet1 action, whole mount in situ hybridization was performed with probes for these growth factor genes. Results of this analysis demonstrated a decrease in expression in each of these genes in isl 1 null mice. Expression of some of these growth factors was severely downregulated or undetectable in regions that overlapped islet1 expression, including expression of BMP4, BMP7, and FGF10. These genes are likely to be direct or indirect targets of Islet. Expression of the other BMP and FGF genes was still present, but the domain of expression was decreased in regions overlapping with islet1 expression, similar to results observed with islet1 mRNA in islet1 mutants. This decrease may reflect a decrease in the number of cells that express these growth factors.

The data described herein demonstrate that progenitors which give rise to the outflow tract also give rise to a majority of cells in both the right ventricle and the atria, and a subset of cells within the left ventricle. Thus, the previously described secondary or anterior heart field is a subset of this progenitor population, which is marked by islet1 expression. Islet1 function is required for these cells to contribute to the heart. In the absence of Islet1, hearts which form are missing segments normally contributed by islet1 expressing progenitors. In distinction, progenitors that will give rise to the majority of cells of the left ventricle and a subset of atrial cells do not express islet1, and are capable of giving rise to cardiac cells of these identities in the absence of Islet1 function.

The appearance and characteristics of the heart in islet1 mutants, and the analysis of islet1 expression and fate mapping of islet1 progenitors, have led to a new working model of heart development. In this model, the first protruding segments of cardiogenic mesoderm at the midline are the first to differentiate, do not express islet1, and will give rise to a majority of cells within the left ventricle and some of the adjacent atrium. Islet1 expressing progenitors migrate in, progressively differentiating and downregulating islet1 expression as they join the "primary" heart segments, to form the majority of cells of the right ventricle, outflow tract, and remainder of the atrium. It should be noted that a substantial number of descendents of islet1 expressing progenitors were found within the left ventricle, at the junctional region with the right ventricle, within trabeculae, and along the wall of the inner curvature, descending slightly into the dorsal wall of the left ventricle.

During earliest stages of heart development, islet cells migrate in throughout the anterior-posterior extent of the myocardium, when adjacent mesenchyme is contiguous with differentiating myocardium. At later stages, islet progenitors migrate into the heart through the two regions which remain connected to the splanchnic mesenchyme of the dorsal body wall. Anteriorly, this is the region of the aortic sac and posteriorly, the dorsal mesocardium.

Previous anatomical analysis of human heart development utilizing molecular markers has indicated that extra-cardiac mesenchyme, which migrates in through the dorsal mesocardium, contributes to both atrial and atrio-ventricular septation (Lamers and Moorman, 2002). There is controversy as to whether the mesenchymal cap on the leading edge of the primary atrial septum originates from this extra-cardiac mesoderm, or derives from cushion endothelium. This question can now be definitively addressed by islet1 lineage analysis. Furthermore, it will be of interest to investigate the role of islet-derived myocardial cells in cardiac septation generally.

It is interesting to note that descendents of islet-expressing progenitors markedly populate regions that coincide with markers of the developing conduction system, indicating that this population may play a major role in conduction system development (Rentschler et al, 2002; Kondo et al, 2003).

The data described herein demonstrate that in the absence of Islet1, islet1 expressing cardiac progenitors do not substantially contribute to the heart, and are decreased in number, demonstrating that Islet1 is required for proliferation and/or survival of these progenitors. The observation that most descendents of islet1 progenitors are not present in hearts of isl 1$^{-/-}$ mutants indicates that Islet1 may also be required for migration.

Islet1 expression is down regulated as precursors differentiate, indicating that, in cardiogenic precursors, Islet function may be required to maintain an undifferentiated state, and/or may be incompatible with a differentiated state. Islet1 is also required for cell survival in motor neurons, but is expressed and functions in differentiated cells (Pfaff et al., 1996). In pancreatic development, Islet1 function is required in both pancreatic mesenchyme, and in differentiated islet cells (Ahlgren et al., 1997).

Growth of the heart following myocyte differentiation has led to the belief that extensive proliferation of differentiated myocytes occurs, to account for myocardial growth. The migration of islet1 expressing precursors into the heart indicates that some growth of the heart can also be accounted for by this migration. However, in islet1 mutants, non-islet expressing progenitors differentiate and undergo an expansion, indicating that both migration and proliferation of differentiated precursors play a role in cardiac growth.

The hearts of islet1 mutants do not appear to have undergone looping morphogenesis, in that the ventricular segment remains anterior to the atrial segment. This observation indicates that migration of islet1 expressing progenitors into the heart is intimately linked to the process of looping morphogenesis. Looping morphogenesis may be a result, not only of myocardial growth, but also of the migration of islet1-expressing cells into the heart.

In addition to being expressed in cardiogenic mesoderm, islet1 is expressed in pharyngeal endoderm, a tissue that has been demonstrated to play an important role in heart development (Lough et al,). This raises the possibility that the requirement for islet in cardiac progenitors may not be cell autonomous. Future experiments will be directed toward this question.

The studies described herein demonstrate that Islet1 defines and is required for one of the cardiogenic fields. It is of interest to understand other genes that may be similarly required for the other, non-islet expressing field. In this context, it should be noted that the Nkx2.5 knockout mouse has a mutant heart that has an outflow tract, right ventricular cells, and atrial cells (Harvey et al, 1999; Tanaka et al, 1999). A number of markers for left ventricular identity are absent, indicating absence of left ventricular identity. These observations raise the possibility that Nkx2.5 is required for formation of cardiac tissue from non-islet expressing progenitors. Nkx2.5 may also play a role in the islet-expressing heart field, although it clearly is not required in the manner that Islet is, given the contrasting phenotypes of islet1 and Nkx2.5 null mice. Creation of mice that are doubly mutant for islet1 and Nkx2.5 can be used to assess these possibilities. It has been shown that islet1 mRNA expression is maintained in Nkx2.5 knockout mice (unpublished observations).

As discussed above, Islet1 positive progenitors may influence cardiac looping morphogenesis. Looping of the heart occurs in a characteristic left-right orientation, with the outflow tract and right ventricle looping rightward. Perturbation of left-right axis information can result in situs inversus of the heart, a leftward looping of the outflow tract and right ventricle. Atrial isomerism can also result. The data described herein demonstrate that the outflow tract, right ventricle, and a majority of atrial cells derive from islet1-expressing progenitors, indicating that left-right information imparted to these precursors will be a critical determinant of left right cardiac asymmetry. Previous analysis of genetic markers has indicated that initial left-right axis information is preserved in the arrangement of the atria, but is rotated in the ventricles. That is, that the "left" and "right" ventricles do not strictly correspond to the left and right body axis (Campione et al., 2001; Franco et al., 2000). Our findings that the left and right ventricles derive from distinct cardiogenic fields gives further insight into this observation. It will be of interest to re-examine left right patterning of the heart in light of the islet1 progenitor population, to investigate genes involved in imparting left right information to these cells prior to their entering the heart, and their subsequent positioning within the heart relative to their original left-right orientation. Similarly, it will be of interest to examine left right identities imparted to non-islet expressing progenitors, and the final positioning of left and right segments within the developed heart.

A homeodomain transcription factor, pitx2, is downstream in the left-right pathway, is specifically expressed in left lateral mesoderm, and remains regionalized with later development (Capdevila et al, 2000). Recent analysis has demonstrated that pitx2 is asymmetrically expressed in the region of the cardiogenic crescent, and later is expressed in left, not right atria, and in distinct portions of the outflow tract, right and left ventricles (Campione et al, 2001). It will be of great interest to investigate potential asymmetric expression of pitx2 in islet-expressing progenitors and perhaps use pitx2 expression as a marker to investigate migratory paths undertaken by islet1-expressing progenitors. In this regard, at ED9.5, pitx2c is expressed asymmetrically in branchial arch and splanchnic mesoderm adjacent to the aortic sac (Liu et al, 2002). Pitx2 knockout mice are nonviable, and display a number of cardiac phenotypes, although hearts still apparently loop to the right (Capdevila et al, 2000). It will be intriguing to re-examine the pitx2 null phenotype, and other issues of left right cardiac asymmetry, within the context of the islet1 paradigm.

Absence of Islet resulted in reduction of the number of islet1 expressing cardiogenic precursors, indicating that growth factor signalling may be perturbed. As both FGF and BMP signalling are required for cardiogenesis (Kirby, 2002; Yutzey and Kirby, 2002), we examined expression of a number of BMP or FGF growth factors which are expressed within or adjacent to islet1 expressing cardiac progenitors. The data described herein demonstrated a significant downregulation or decrease in each growth factor examined, selectively in regions which overlap with islet1 expressing cardiogenic precursors.

Islet1 mutants exhibited an overall reduction in the domain of fgf8 expression, but their phenotype was more severe than that seen with fgf8 hypomorphs. Mouse knockouts of fgf4 or fgf8 are early embryonic lethal, but mice which are hypomorphic for fgf8 die neonatally due to cardiovascular defects, including malformations of the outflow tract (Abu-Issa et al., 2002; Feldman et al., 1995; Frank et al., 2002; Sun et al., 1999). In islet1 mutants, fgf10 expression was virtually absent in islet1-expressing cardiogenic precursors. Mouse knockouts of fgf10 die neonatally, which has been ascribed to their lung phenotype (Sekine et al., 1999). However, there may be an as yet undescribed cardiac phenotype, albeit clearly not as severe as the islet cardiac phenotype.

BMP4 and BMP7 are co-expressed in a highly overlapping manner with islet1 expressing cardiogenic precursors. BMP2 and BMP6 are expressed in a distinctive manner from BMP4, BMP7, or each other, but their expression also overlaps with that of islet1. In islet1 mutants, expression of each of these growth factors was greatly reduced or absent in regions coincident with islet1 expression. Knockouts of each of these BMPs have been made, and double knockouts of BMP6/7 have been made (Kim et al., 2001; Winnier et al., 1995; Zhang and Bradley, 1996). None of these mutants recapitulates the cardiac phenotype of the islet1 mutant, due to earlier defects in implantation or gastrulation, or, if they survive the earlier defects, potentially due to functional redundancy.

Our results indicate that the cardiac phenotype in islet1 mutants may be all or in part due to defects in either FGF or BMP signalling, or both. Discriminating between these possibilities will require future experiments to ablate these signalling pathways in islet1 expressing progenitors. Additionally, other growth factor pathways may be affected in islet1 mutants.

Expression of islet1 in the splanchnic mesoderm of the pharyngeal and foregut region is intriguing in view of a number of experiments which have indicated that the vertebrate heart has evolved from pharyngeal or gut mesoderm (Haun et al., 1998; Park et al., 1998; Ranganayakulu et al., 1998). Previous data has demonstrated that islet1 is expressed in cardiogenic precursors in chick (Yuan and Schoenwolf, 2000). There is a *Drosophila* homologue of islet which, as for mouse islet1, has a role in motor neuron development, and, intriguingly, is expressed in the dorsal vessel (Thor and Thomas, 1997). It will be of great interest to examine the role of islet in cardiogenesis in other species, to gain further insight into cardiac evolution. Results may indicate that islet-expressing progenitors are, in evolutionary terms, "primary". If this were the case, it might indicate that the left ventricle was a later evolutionary development. Interestingly, in zebrafish, which have a single ventricle, DHand, a marker of right ventricle in higher vertebrates, is present, whereas no orthologue of its left ventricular counterpart, EHand has been found (Angelo, Lohr, Lee, Ticho, Breitbart, Yost, 2000).

Perhaps one of the most exciting aspects of our discovery of the role of Islet in cardiogenesis is the prospect of utilizing Islet1 as a marker for the cardiogenic stem cell state. A stem cell can be defined as a progenitor cell which can proliferate and give rise to a number of distinct lineages. Islet1-expressing cells conform to this definition, giving rise to a number of distinct cardiac lineages. The unique property of islet1 in being expressed in cells prior to differentiation should allow for cell sorting on the basis of islet1 expression. Additionally, Islet1's role in dictating the proliferation and/or survival of these cells indicate that Islet1, in concert with other factors, may be utilized to drive a cardiogenic stem cell state.

Based on these considerations outlined above, a rare cell population was identified within mouse, rat and human non-myocyte cell cultures, that can be expanded and propagated in vitro. These cells differentiate not only into mesodermal lineages but also neuroectoderm. We are able to show that cells capable of differentiating in vitro to cells of at least two germ layers can be selected from rodent and human hearts. Islet-1 (isl 1), a LIM-homeodomain transcription factor, marks these undifferentiated progenitor cells and allows a visualization of this cardiogenic precursor population in the adult heart. Therefore these cells were termed i-cells.

Culturing of undifferentiated i-cells, as set forth in Example 1 below, revealed that the cardiogenic precursor population could only be cultured without differentiation and senescence on a feeder layer of species-specific cardiac fibroblasts. Similar feeder-dependent culture conditions are used for the isolation of mouse and human ES cells and such feeder layers proved to be critical to maintaining them in an undifferentiated state (Donovan and Gearhart, 2001).

The requirement for feeder cells or conditioned medium from cardiac fibroblasts indicates that they provide factors that suppress the differentiation or promote the self-renewal of the multipotent progenitor cells. An activity with these properties is referred to as differentiation-inhibiting activity of i-cells (DIAI). For murine ES cells, leukaemia inhibitory factor (LIF), a member of the cytokine family related to interleukin-6, can replace the requirement for feeder cells (Nichols, et al., 1990). For inhibiting murine ES cell differentiation activation of the signaling component of the LIF receptor, glycoprotein 130 (gp 130), is both necessary and sufficient. However, human ES cells and cardiac i-cells do not seem to require LIF for blocking differentiation and stimulating self-renewal (Thomson, et al., 1998).

Until now no in vitro culture conditions have been established that allow multipotent, adult stem cells to be expanded and propagated. dult HSCs or NSCs, in vivo defined as long-term repopulating cells, cannot be expanded in culture without losing developmental potential (Weissman, 2000). But one recent study shows that mesenchymal stem cells derived from the bone marrow, can be grown under special conditions indefinitely in culture (Jiang, et al., 2002).

The invention also provides a cellular composition comprising an enriched population of isl 1 positive stem cells. The composition preferably contains a majority of or at least about 90% isl 1 positive stem cells as compared with other cell types. The isl 1 positive stem cells are derived from any cardiac tissue, such as from a rat, mouse or human.

As phenotypic characteristics of an undifferentiated state, it has been discovered that i-cells express high levels of isl 1 in the nucleus and nestin, an intermediate filament that marks undifferentiated NSCs, in the cytosol. Additionally, cells showed lower expression of Nkx2.5, a homeobox vertebrate homologue of *Drosophila* tinman, and the ES cell transcription factor oct-4. Thus, these markers are useful for identifying i-cells.

Isl 1 is essential for motor neuron and pancreatic development (Pfaff, et al., 1996). Homozygous knock-out embryos for isl 1 die around ED 10.5, because of a univentricular, undivided heart-chamber and vascular abnormalities of the outflow tract (Cai, et al., 2003). Lineage analysis of isl 1 expressing cells revealed that these cells substantially contribute to the embryonic heart, comprising a majority of cells in the outflow tract, right ventricle and both atria (Cai, et al., 2003). The downregulation of isl 1 expression in the neonatal and adult heart allows a visualization of cardiogenic precursors in the myocardium.

Immunohistochemistry showed isl 1 expressing cells in the adult heart mainly localized in the right ventricle, septum and atria. In undifferentiated precursor cells isl 1 is highly expressed in the nucleus and is downregulated during differentiation of i-cells. Islet expression marks a cardiogenic stem cell population in vitro and in vivo and appears to be required for differentiation and survival of these stem cells.

Nkx2.5 is also expressed in i-cells in an undifferentiated state. This transcription factor is one of the earliest markers of vertebrate heart development and is important for the regulation of cardiac-restricted gene activity. The POU-domain transcription factor oct-4 is a molecular marker for pluripotent ES cells. Oct-4 is expressed in the pre-gastrulation embryo, early cleavage-stage embryo, cells of the inner cell mass of the blastocyst and in embryonic carcinoma cells. In the adult animal oct-4 is only found in germ cells and mesenchymal stem cells (Rosner, et al., 1990).

By the present in invention, a novel cardiac progenitor population has been discovered, isolated and characterized. Isl 1 expression marks these cardiogenic stem cells and appears to be required for the differentiation state and survival of these cells. These cells are useful to study and understand signalling pathways of cardiac stem cell differentiation and growth, paving the way for future therapeutic applications for congenital and adult heart disease.

Gene targeting in i-cells with further differentiation in neurons or myocytes allows studies in cell biology without having to struggle with the complexity of time consuming animal models. The aim of cell culture is to develop well defined and easily manipulated experimental systems that offer the advantages of clonal homogeneity and the ability to manipulate external environments. Furthermore, due to the ethical unacceptability of experimentally altering the human germ line, the ES cell transgenic route is not available for experiments that involve manipulation of human genes. Gene targeting in human i-cells allows important applications in areas where rodent model systems do not adequately recapitulate human biology or disease processes.

In addition, I-cells can be useful as a source of donor tissue for cardiac and neuronal cell therapy. Early embryonic stem cells have disadvantages for cell-based therapy: (i) the number of transformations and (ii) the complexity of signals required to achieve a specific differentiated phenotype. Instead, the phenotypic differentiation of developing i-cells and adult-derived cardiac progenitors circumvent both ethical and immunological constraints.

Cross-lineage transformation of i-cells offers a new avenue for a more flexible tissue source, in particular to derive autografts from patients themselves. A further advance of i-cells compared to ES cells is that these precursor cells are less immunogenic than primary embryonic myocytes in xenografts, highlighting a way to overcome one of the main difficulties of transplantation from non-human donors.

The invention methods utilize isolated monoclonal antibodies characterized as specifically binding to Islet 1 polypeptide and immunoprecipitating the Islet 1 polypeptide Any suitable immunoassay format known in the art and as described herein can be used to detect the presence of and/or quantify the amount of Islet 1-expressing cells in a diverse population of cells. Although any type of anti-Islet 1 polypeptide antibody, as described herein, which binds specifically to Islet 1 polypeptide, can be used in the invention methods, monoclonal antibodies are preferred.

The invention immunological tests for Islet 1 polypeptide can be used in a high throughput format using any technique known in the art, such as FASC screening as is described below in greater detail.

Detectable labels suitable for binding to antibodies used in the invention methods, including high throughput screening formats, include radiolabels linked to the antibodies using various chemical linking groups or bifunctional peptide linkers. A terminal hydroxyl can be esterified with inorganic acids, e.g., $^{32}$P phosphate, or $^{14}$C organic acids, or else esterified to provide linking groups to the label. Enzymes of interest as detectable labels will primarily be hydrolases, particularly esterases and glycosidases, or oxidoreductases, particularly peroxidases. Fluorescent compounds include fluorescein and its derivatives, rhodamine and its derivatives, dansyl, umbelliferone, and so forth. Chemiluminescers include luciferin, and 2,3-dihydrophthalazinediones (e.g., luminol), and the like.

Antibodies may also be attached to solid supports, which are particularly useful for immunoassays or immunoprecipitation of Islet 1 polypeptide. Such solid supports include, but are not limited to, glass, cellulose, polyacrylamide, nylon, polystyrene, polyvinyl chloride or polypropylene, for example protein G covered wells of microtiter plates or beads.

Antibodies directed against a specific epitope, or combination of epitopes, so as to bind specifically with the Islet 1 polypeptide will allow for the screening of cell populations as described herein. Various screening techniques can be utilized using such monoclonal antibodies, and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737-49 (1999)).

The antibodies useful in the invention methods may be assayed for immunospecific binding by any method known in the art. The immunoassays which can be used, include but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., Western blot analysis. Those of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or 125 I) diluted in blocking buffer, washing the membrane in wash buffer, and detecting the presence of the antigen. Those of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. Those of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^{3}$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with the antibody of interest conjugated to a labeled compound (e.g., $^3$H or $^{125}$I) in the presence of increasing amounts of an unlabeled second antibody.

Antibodies used in invention assay(s) can be polyclonal, monoclonal, or a functionally active fragment thereof. Mono- or poly-clonal antibodies to a islet 1 polypeptide are raised in appropriate host animals by immunization with immunogenic conjugate(s) using conventional techniques as are known in the art.

The preparation of monoclonal antibodies is disclosed, for example, by Kohler and Milstein, Nature 256:495-7, 1975; and Harlow et al., in: Antibodies: a Laboratory Manual, page 726 (Cold Spring Harbor Pub., 1988), which are hereby incorporated by reference. Briefly, monoclonal antibodies can be obtained by injecting mice, or other small mammals, such as rabbits, with a composition comprising an invention immunogenic conjugate whose preparation is disclosed above, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, for example, Barnes et al., Purification of Immunoglobulin G (IgG), in: Methods in Mol. Biol., 10: 79-104, 1992). Antibodies of the present invention may also be derived from subhuman primate antibodies. General techniques for raising antibodies in baboons can be found, for example, in Goldenberg et al., International Patent Publication WO 91/11465 (1991) and Losman et al., Int. J. Cancer, 46:310-314, 1990.

It is also possible to use anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

The term "antibody" as used in this invention includes intact molecules as well as functional fragments thereof, such as Fab, F(ab')$_2$, and Fv that are capable of binding islet 1 polypeptide These functional antibody fragments are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference). As used in this invention, the term "epitope" means any antigenic determinant on an antigen to which the paratope of an antibody binds. Epitopic determinants usually consist of chemically active surface groupings of molecules such as amino acids or carbohydrate side chains and usually have specific three dimensional structural characteristics, as well as specific charge characteristics.

Antibody fragments according to the present invention can be prepared by proteolytic hydrolysis of the antibody or by expression in E. coli of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of V$_H$ and V$_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise V$_H$ and V$_L$ chains connected by a peptide linker. These single-chain antigen binding proteins (sFv) are prepared by constructing a structural gene comprising DNA sequences encoding the V$_H$ and V$_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

The invention methods use monoclonal antibodies characterized as specifically binding to islet 1 polypeptide, wherein Islet 1 polypeptide retains functional activity.

Hybridoma cell lines producing monoclonal antibodies useful in the invention methods for immunocapture of Islet 1 polypeptide are commercially available.

The following examples are intended to illustrate but not limit the invention.

Example 1

Experimental Procedures

Mouse Mutants

The generation of islet null mutants has been previously described (Pfaff et al, 1996). The knockout construct deleted the exon encoding the second LIM domain of Islet 1. Islet1-cre mice were generously provided by Thomas M. Jessell, and have been previously described (Srinivas et al, 2001). An IRES-cre cassette was inserted into the exon encoding the second LIM domain of Islet1, disrupting islet gene expression.

Whole Mount RNA In Situ Hybridization

Whole mount RNA in situ hybridization was carried out as previously described (Wilkinson, 1999). References for specific RNA probes which were used are as follows: MLC2a (Kubalak et al., 1994); MLC2v (O'Brien et al., 1993); tbx5 (Bruneau et al., 1999); tbx20 (unpublished results); BMP2, BMP6, BMP7 BMP4, BMP5 (Kim et al., 2001; Lyons et al., 1995); FGF4, FGF8 and FGF10 (Feldman et al., 1995; Sun et al., 1999); EHand (Cross et al., 1995); islet1 (EST, GenBank Accession No.: AA198791)(SEQ ID NO:2); msx2 (Liu et al., 1994).

Double RNA in situ hybridization was performed utilizing digoxigenin and fluorescein-labeled probes that were conjugated with alkaline phosphatase (Roche Cat. #1277073, 1685619). Staining reactions were performed with CIP/Ferricyanide/Ferrocyanide according to Janet Rossant's lab protocols website on the worldwide web (mshri.on.ca/rossant/protocols/doubleINsitu) and MagentaPhos-tet Red according to Claudio Stern's lab protocols website (sternlab.anat.ucl.ac.uk/INSITU), or with Fast Red (Roche Cat. No.: 1496549) and BCIP (a chromogenic substrate for alkaline phosphatases) alone. After incubation with and staining to detect the first antibody (Anti-Fluorescein-AP, Roche Cat. No.: 1426338), embryos were incubated at 65° C. for 1 hour to inactivate alkaline phosphatase activity, and washed before incubating with and staining to detect the second antibody (Anti-Digoxigenin-AP, Roche Cat. No.: 1093274). For embryos stained with Fast Red, which is soluble in alcohol, cryosections were prepared. For embryos stained with BCIP/Ferricyanide/Ferrocyanide and MagentaPhos-tet Red, paraffin sections were prepared, with brief washes in alcohol to minimize loss of signal.

Scanning Electron Microscopy

A standardized procedure for scanning electron microscopy (SEM) of the heart was utilized (Pexieder, 1986). Briefly, embryos were submitted to ethanol dehydration and critical point drying from Freon 113 to Freon 23. Dried specimens were mounted on SEM tubes, ion sputtered with 300 nm gold, and examined in the scanning electron microscope. SEM photomicrographs were taken in standard orientations and magnifications.

Example 2

Culture of Undifferentiated I-Cells

To isolate cardiac progenitors from murine hearts, the methods used were similar to those used for cardiomyocyte isolations from the adult organ. In a trypsin-digested state i-cells and cardiac fibroblasts share a similar cell diameter of around 35 μm and copurify in the same fractions on Percoll gradients. I-cell cultures were developed by testing multiple conditions, including cultures on fibronectin, collagen-type-IV or laminin. Media conditions tested included several concentrations of fetal calf serum (FCS), epidermal growth factor (EGF), platelet derived growth factor (PDGF-BB), acidic fibroblast growth factor (aFGF), basic fibroblast growth factor (bFGF), bone morphogenetic protein (BMP) 2+4, insulin-like growth factor (IGF) 1, sonic hedgehoc (Shh) and dexamethasone, as set forth below.

Approximately 5-10% of 96-well plates seeded with 10 isl 1 positive cells yielded continuous growing cultures, indicating that only around 5-10 cells out of 100 i-cells are capable of initiating i-cell cultures. Several i-cell populations have now been cultured for more than 12 population doublings. It was discovered that the cardiogenic precursor population can only be cultured without differentiation or cell death on a feeder layer of cardiac fibroblasts or in conditioned medium of freshly isolated fibroblasts from the heart. Differentiation of I-cells into myocytes and neurons can be induced by withdrawal of conditioned medium from cardiac fibroblasts or separation of I-cells from the feeder layer. The morphology and phenotype were similar after 5 to more than 10 population doublings.

I-cells were ~35 μm in diameter with a large nucleus and a scant cytoplasm growing in three-dimensional spheres always attached to the fibroblastic feeder layer. Similar results were obtained when i-cells from atria of human tissue were isolated and cultured.

Example 3

In vitro Differentiation of Single I-Cells

Next in vitro differentiation capacity of i-cells obtained from mouse and rat hearts was tested by adding cytokines chosen on the basis of what has been reported for ES cell differentiation to neuroectoderm and mesoderm. Differentiation required that i-cells had to be replated without a feeder layer at a density around $1-2 \times 10^4$ cells $cm^{-2}$ in medium containing no serum, but lineage-specific cytokines. Neuroprogenitors can be expanded with PDGF-BB and induced to differentiate by addition of bFGF (Palmer, et al., 1999).

Under the bFGF treatment around 45% of the i-cells acquired morphologic and phenotypic characteristics of astrocytes with immunohistochemical positivity for glial acidic fibrillary protein (GFAP) and neurons which stained positive for neurofilament 200 (NF-200). Myocytic differentiation acquired cells that showed positive signals for α-sarcomeric actin and α-actinin in immunohistochemical experiments.

Example 4

Isolation Protocol for Postnatal Cardiac Progenitor Cells from Mouse Hearts 35 to 50 hearts of 1 day old mouse pups were dissected out of the thoraxaperture, cut into four pieces and washed 3× in HBSS (Hank's balanced salt) solution without $Ca^{2+}$ at 4° C. The hearts were transferred into 0.5 mg/ml trypsin-HBSS solution and predigested overnight (~17 hours) at 4° C. on an orbital shaker. Half of the trypsin solution was removed from the predigested tissue and the remaining part diluted 1:1 with warm DMEM/M199 cell culture medium (4:1 ratio) containing penicillin (100 U/ml)/streptomycin (100 mg/ml)/HEPES (25 mM)/glutamine (2 mM).

After shaking the tissue for 3-4 min at 37° C. the diluted trypsin was removed from the tissue and 20 ml of 24 U/ml collagenase type II in HBSS added to the tissue solution. After an incubation of 2 min in a shaking water bath at 37° C., the initial collagenase type II digest is discarded, as it mainly contains red blood cells and dead tissue cells. The tissue was resuspended in 12 ml of fresh collagenase type II and shaken for 10 min in a water bath at 37° C. The supernatant was inactivated by addition of the same volume of cold DMEM/M199 medium containing 10% horse serum and 5% fetal bovine serum and stored on ice. The resuspension of the tissue and the inactivation of the supernatant was repeated three more times until the tissue pieces were completely digested. The supernatants from the digests were pulled together and centrifugated at 800 rpm for 5 min. The supernatant contained most of the mesenchymal cells of the heart and the pellet most of the cardiac myocytes.

After a second centrifugation at 1500 rpm for 3 min, the mesenchymal cells were sequentially plated for 20 min on plastic in DMEM containing penicillin (100 U/ml)/streptomycin (100 mg/ml)/HEPES (25 mM)/glutamine (2 mM)/10% new born calf serum and 5% fetal bovine serum. After 20 min, the non-attached cells were removed from the plates by two rigorous washing steps with PBS.

The attached cardiac mesenchymal cells were cultured for 14-21 days at 37° C. with 5% $CO_2$. Culture medium was changed to DMEM/F12 containing B27 supplement, 2% fetal bovine serum, 10 ng/ml EGF at the second day in culture when the cells reached confluency. After 10 days the cardiac progenitor population started to propagate on top of the feeder layer of the mesenchymal cells of the heart.

Example 5

Isolation Protocol for Postnatal Cardiac Progenitor Cells from Rat Hearts 50 hearts of postnatal day 1-5 rat pups were dissected out of the thorax, cut into four pieces and washed 2× in the ADS buffer containing 6.8 g/l NaCl, 4.7 g/l HEPES, 0.12 g/l $NaH_2PO_4$, 0.14 g/l $NaH_2PO_4H_2O$, 1 g/l glucose, 0.4 g/l KCl, 0.2 g/l $MgSO_47H_2O$ (pH adjustment to 7.35). The heart pieces were incubated for 15 min at 37° C. in ADS buffer containing collagenase type II (115 units/ml) and pancreatin (0.8 mg/ml) in a stir flask. The first digest was discarded. 18 ml of fresh enzyme solution were added to the tissue and stirred for 20 min at 37° C.

After the 20 min digestion, the enzyme solution was removed and inactivated with 6 ml of neonatal calf serum. Fresh enzyme solution was added to the tissue pieces in the stirring flask and incubated for another 20 min at 37° C. The digest from the first 20 minute digestion was centrifuged at 1000 rpm for 6 min, the pellet resuspended in 5 ml of neonatal calf serum and placed at 37° C. in 10% $CO_2$. The above steps, from removal of the enzyme solution to resuspension of the pellet was repeated four times.

The resulting cell suspensions from each centrifugation were pooled and the pool was centrifuged at 1000 rpm for 6 min. The pellet was resuspended in 12 ml of ADS buffer. The cell suspension was layered on the top of a Percoll gradient (2 ml cells per each gradient). Each Percoll gradient consists of 4 ml Percoll 1.06 g/ml as the top layer and 3 ml Percoll 1.08 g/ml as the bottom layer.

After centrifugation at 3000 rpm for 30 min with low acceleration and deceleration, the upper band consisted of the cardiac mesenchymal cells, the middle band at the interphase consisted of the cardiac myocytes. The mesenchymal cells were collected with a Pasteur pipette.

After a second centrifugation at 1500 rpm for 3 min, the mesenchymal cells were sequentially plated for 20 min on plastic in DMEM containing penicillin (100 U/ml)/streptomycin (100 mg/ml)/HEPES (25 mM)/glutamine (2 mM)/10% new born calf serum and 5% fetal bovine serum. 20 min later the non-attached cells were removed from the plates by two rigorous washing steps with PBS.

The cardiac mesenchymal cells were cultured for 14-21 days at 37° C. with 5% $CO_2$. Culture medium was exchanged to DMEM/F12 containing B27 supplement, 2% fetal bovine serum, 10 ng/ml EGF at the second day in culture when the cells reached confluency. After 10 days, the cardiac progenitor population started to propagate on top of the feeder layer of the mesenchymal cells of the heart.

Example 6

FACS Analysis of Phenotypic Cell Markers of the Cardiac Progenitor Cell Population The phenotypic cell markers of the isolated cells from postnatal mouse and rat myocardium in Example 4 and Example 5 above, respectively, were characterized by FACS analysis. The FACS analysis showed that: 90% of the cells express the LIM homeodomain transcription factor islet1; ~90% of the cells coexpress the *Drosophila* tinman homologue Nkx2.5; and 30-40% of the cells coexpress the intermediary filament nestin.

Example 7

Differentiation Protocols

For differentiation of the progenitor population, the cells were replated without the feeder layer of mesenchymal cells at a density around $2 \times 10^4$ cells per $cm^{-2}$ in a medium containing 2% of fetal calf serum and the lineage-specific differentiating agents.

In vitro myocytic differentiation was performed with conditioned medium enriched for wnt11 of a retrovirally infected NIH3T3 cell line, which stably expresses and secretes wnt11. Cells were treated with a sequential differentiation protocol for 4.5 days with wnt11 conditioned medium on fibronectin coated culture dishes and afterwards with BMP2 in a concentration of 2.5 ng/ml. Thereafter differentiated cells were analyzed in single cell experiments for channel currents in an electrophysiological setting and for intracellular $Ca^{2+}$ transients.

In vitro differentiation in neuronal cell types was performed with 0.2 µM all-trans retinoic acid and 5 µM forskolin for 10-15 days in laminin and polylysin coated culture dishes.

In vitro differentiation in adipocytes was performed with 10% neonatal calf serum and 5% fetal bovine serum in plastic culture dishes.

Although the invention has been described with reference to the above examples, it will be understood that modifications and variations are encompassed within the spirit and scope of the invention. Accordingly, the invention is limited only by the following claims.

REFERENCES

1. Abu-Issa, R., Smyth, G., Smoak, I., Yamamura, K., and Meyers, E. N. (2002). Fgf8 is required for pharyngeal arch and cardiovascular development in the mouse, Development 129, 4613-25.
2. Ahlgren, U., Pfaff, S. L., Jessell, T. M., Edlund, T., and Edlund, H. (1997). Independent requirement for ISL 1 in formation of pancreatic mesenchyme and islet cells, Nature 385, 257-60.
3. Brazelton, T. R., et al. (2000). From marrow to brain: expression of neuronal phenotypes in adult mice. Science 290, 1775-1779.
4. Brown, J. P., et al. (1997) Bypass of senescence after disruption of $p21^{CIP1/WAF1}$ gene in normal diploid human fibroblasts. Science 277, 831-834.
5. Bruneau, B. G., Logan, M., Davis, N., Levi, T., Tabin, C. J., Seidman, J. G., and Seidman, C. E. (1999). Chamber-specific cardiac expression of Tbx5 and heart defects in Holt-Oram syndrome, Dev Biol 211, 100-8.
6. Cai, C., et al. (2003). Islet1, a LIM-homeodomain transcription factor, redefines cardiogenic fields and delineates a novel cardiac stem cell population. submitted.
7. Campione, M., Ros, M. A., Icardo, J. M., Piedra, E., Christoffels, V. M., Schweickert, A., Blum, M., Franco, D., and Moorman, A. F. (2001). Pitx2 expression defines a left cardiac lineage of cells: evidence for atrial and ventricular molecular isomerism in the iv/iv mice, Dev Biol 231, 252-64.
8. Carson, C. T., Kinzler, E. R., and Parr, B. A. (2000). Tbx12, a novel T-box gene, is expressed during early stages of heart and retinal development, Mech Dev 96, 137-40.
9. Clarke, D., et al. (2000) Generalized potential of adult neural stem cells. Science 288, 1660-1663.
10. Cross, J. C., Flannery, M. L., Blanar, M. A., Steingrimsson, E., Jenkins, N. A., Copeland, N. G., Rutter, W. J., and Werb, Z. (1995). Hxt encodes a basic helix-loop-helix transcription factor that regulates trophoblast cell development, Development 121, 2513-23.
11. Crossley, P. H., and Martin, G. R. (1995). The mouse Fgf8 gene encodes a family of polypeptides and is expressed in regions that direct outgrowth and patterning in the developing embryo, Development 121, 439-51.
12. Cserjesi, P., Brown, D., Lyons, G. E., and Olson, E. N. (1995). Expression of the novel basic helix-loop-helix gene eHAND in neural crest derivatives and extraembryonic membranes during mouse development, Developmental Biology 170, 664-78.
13. de la Cruz, M. V., and Sanchez-Gomez, C. (2000). Straight Heart Tube. Primitive Cardiac Cavities vs. Primitive Cardiac Segments. In Living Morphogenesis of the Heart, M. V. de La Cruz, and Markwald, R. R., ed. (Boston, Basel, Berlin, Birkhauser), pp. 85-99.
14. Donovan, P. J. & Gearhart, J. (2001). The end of the beginning for pluripotent stem cells. Nature 414, 92-97.
15. Dudley, A. T., and Robertson, E. J. (1997). Overlapping expression domains of bone morphogenetic protein family members potentially account for limited tissue defects in BMP7 deficient embryos, Developmental Dynamics 208, 349-62.
16. Evans, M. J. & Kaufmann, M. H. (1981). Establishment in culture of pluripotential cells from mouse embryos. Nature 292, 154-156.
17. Feldman, B., Poueymirou, W., Papaioannou, V. E., DeChiara, T. M., and Goldfarb, M. (1995). Requirement of FGF-4 for postimplantation mouse development, Science 267, 246-9.
18. Franco, D., Campione, M., Kelly, R., Zammit, P. S., Buckingham, M., Lamers, W. H., and Moorman, A. F. (2000). Multiple transcriptional domains, with distinct left and right components, in the atrial chambers of the developing heart, Circ Res 87, 984-91.
19. Franco, D., Markman, M. M., Wagenaar, G. T., Ya, J., Lamers, W. H., and Moorman, A. F. (1999). Myosin light chain 2a and 2v identifies the embryonic outflow tract myocardium in the developing rodent heart, Anat Rec 254, 135-46.
20. Frank, D. U., Fotheringham, L. K., Brewer, J. A., Muglia, L. J., Tristani-Firouzi, M., Capecchi, M. R., and Moon, A. M. (2002). An Fgf8 mouse mutant phenocopies human 22q11 deletion syndrome, Development 129, 4591-603.
21. Friedrich, G. & Soriano, P. (1991) Promoter traps in embryonic stem cells: a genetic screen to identify and mutate developmental genes in mice. Genes Dev. 5, 1513.
22. Gage, F. H. (2000). Mammalian neural stem cells. Science 287, 1433-1438.
23. Geiger, et al. (1998) Globin gene expression is reprogrammed in chimeras generated by injecting adult hematopoietic stem cells in mouse blastocysts. Cell 93, 1055.
24. Gussoni, E. et al. (1999). Dystrophin expression in the mdx mouse restored by stem cell transplantation. Nature 401, 390-394.
25. Haun, C., Alexander, J., Stainier, D. Y., and Okkema, P. G. (1998). Rescue of Caenorhabditis elegans pharyngeal development by a vertebrate heart specification gene, Proceedings of the National Academy of Sciences of the United States of America 95, 5072-5.
26. Hoffman, J. I., and Kaplan, S. (2002). The incidence of congenital heart disease, J Am Coll Cardiol 39, 1890-900.
27. Jackson, K., et al. (2001). Regeneration of ischemic cardiac muscle and vascular endothelium by adult stem cells. J. Clin. Invest. 107, 1395-1402.
28. Jiang, Y., et al. (2002). Pluripotency of mesenchymal stem cells derived from adult marrow. Nature 418, 41-49.
29. Joyner, A. L., Ed. (1998) Gene targeting. A practical approach. Oxford University Press, Oxford.
30. Kaufman, M. H. (1999). The Atlas of Mouse Development, Academic Press).
31. Kelly, R. G., and Buckingham, M. E. (2002). The anterior heart-forming field: voyage to the arterial pole of the heart, Trends Genet 18, 210-6.
32. Kelly, R. G., Brown, N. A., and Buckingham, M. E. (2001). The arterial pole of the mouse heart forms from Fgf10-expressing cells in pharyngeal mesoderm, Dev Cell 1, 435-40.
33. Kim, R. Y., Robertson, E. J., and Solloway, M. J. (2001). Bmp6 and Bmp7 are required for cushion formation and septation in the developing mouse heart, Dev Biol 235, 449-66.
34. Kirby, M. L. (2002). Molecular embryogenesis of the heart, Pediatr Dev Pathol 5, 516-43.

35. Kraus, F., Haenig, B., and Kispert, A. (2001). Cloning and expression analysis of the mouse T-box gene tbx20, Mech Dev 100, 87-91.
36. Krause, D. S., et al. (2001). Multi-organ, multi-lineage engraftment by a single bone-marrow-derived stem cell. Cell 105, 369-377.
37. Kubalak, S. W., Miller-Hance, W. C., O'Brien, T. X., Dyson, E., and Chien, K. R. (1994). Chamber specification of atrial myosin light chain-2 expression precedes septation during murine cardiogenesis, Journal of Biological Chemistry 269, 16961-70.
38. Liu, Y. H., Ma, L., Wu, L. Y., Luo, W., Kundu, R., Sangiorgi, F., Snead, M. L., and Maxson, R. (1994). Regulation of the Msx2 homeobox gene during mouse embryogenesis: a transgene with 439 bp of 5' flanking sequence is expressed exclusively in the apical ectodermal ridge of the developing limb, Mech Dev 48, 187-97.
39. Lyons, K. M., Hogan, B. L., and Robertson, E. J. (1995). Colocalization of BMP 7 and BMP 2 RNAs indicates that these factors cooperatively mediate tissue interactions during murine development, Mech Dev 50, 71-83.
40. Mjaatvedt, C. H., Nakaoka, T., Moreno-Rodriguez, R., Norris, R. A., Kern, M. J., Eisenberg, C. A., Turner, D., and Markwald, R. R. (2001). The outflow tract of the heart is recruited from a novel heart-forming field, Dev Biol 238, 97-109.
41. Nichols, et al. (1990). Establishment of germ-line-competent embryonic stem (ES) cells using differentiation inhibiting activity. Development 110, 1341-1348.
42. Niswander, L., and Martin, G. R. (1992). Fgf-4 expression during gastrulation, myogenesis, limb and tooth development in the mouse, Development 114, 755-68.
43. O'Brien, T. X., Lee, K. J., and Chien, K. R. (1993). Positional specification of ventricular myosin light chain 2 expression in the primitive murine heart tube, Proc Natl Acad Sci USA 90, 5157-61.
44. Orlic, D., et al. (2001). Bone marrow cells regenerate infracted myocardium. Nature 410, 701-705.
45. Palmer, T. D., et al. (1999). Fibroblast growth factor-2 activates a latent neurogenic program in neural stem cells from diverse regions of the adult CNS. J. Neurosci. 19, 8487-8497.
46. Park, M., Lewis, C., Turbay, D., Chung, A., Chen, J. N., Evans, S., Breitbart, R. E., Fishman, M. C., Izumo, S., and Bodmer, R. (1998). Differential rescue of visceral and cardiac defects in Drosophila by vertebrate tinman-related genes, Proceedings of the National Academy of Sciences of the United States of America 95, 9366-71.
47. Pexieder, T. (1986). Standardized method for study of normal and abnormal cardiac development in chick, rat, mouse, dog, and human embryos., Teratology 33, 91C-92C.
48. Pfaff, S. L., Mendelsohn, M., Stewart, C. L., Edlund, T., and Jessell, T. M. (1996). Requirement for LIM homeobox gene Isl 1 in motor neuron generation reveals a motor neuron-dependent step in interneuron differentiation, Cell 84, 309-20.
49. Rafii, S., et al. (1994). Isolation and characterization of human bone marrow microvascular endothelial cells: hematopoietic progenitor cell adhesion. Blood 84, 10-19.
50. Ranganayakulu, G., Elliott, D. A., Harvey, R. P., and Olson, E. N. (1998). Divergent roles for NK-2 class homeobox genes in cardiogenesis in flies and mice, Development 125, 3037-48.
51. Rosner, M. H., et al. (1990). A POU-domain transcription factor in early stem cells and germ cells of the mammalian embryo. Nature 345, 686-692.
52. Sedivy, J. M. & Dutriaux, A. (1999) Gene targeting and somatic cell genetic. Trends in Genetics 15, 88-92.
53. Sedivy, J. M. & Joyner, A. (1992) Gene targeting. WH Freeman Press.
54. Sekine, K., Ohuchi, H., Fujiwara, M., Yamasaki, M., Yoshizawa, T., Sato, T., Yagishita, N., Matsui, D., Koga, Y., Itoh, N., and Kato, S. (1999). Fgf10 is essential for limb and lung formation, Nat Genet 21, 138-41.
55. Soriano, P. (1999). Generalized lacZ expression with the ROSA26 Cre reporter strain, Nat Genet 21, 70-1.
56. Srinivas, S., Watanabe, T., Lin, C. S., William, C. M., Tanabe, Y., Jessell, T. M., and Costantini, F. (2001). Cre reporter strains produced by targeted insertion of EYFP and ECFP into the ROSA26 locus, BMC Dev Biol 1, 4.
57. Sun, X., Meyers, E. N., Lewandoski, M., and Martin, G. R. (1999). Targeted disruption of Fgf8 causes failure of cell migration in the gastrulating mouse embryo, Genes Dev 13, 1834-46.
58. Thomas, T., Yamagishi, H., Overbeek, P. A., Olson, E. N., and Srivastava, D. (1998). The bHLH factors, dHAND and eHAND, specify pulmonary and systemic cardiac ventricles independent of left-right sidedness, Developmental Biology 196, 228-36.
59. Thomson, J. A., et al. (1998). Embryonic stem cell lines derived from human blastocysts. Science 282, 1145-1147.
60. Thor, S., and Thomas, J. B. (1997). The Drosophila islet gene governs axon pathfinding and neurotransmitter identity, Neuron 18, 397-409.
61. Tisdale, J. F. & Dunbar, C. E. (2002). Plasticity and hematopoiesis: Circe's transforming potion? Curr. Opin. Hematol. 9, 268-273.
62. Toma, J. G., et al. (2001). Isolation of multipotent adult stem cells from the dermis of mammalian skin. Nat. Cell. Biol. 3, 778-784.
63. Waldo, K. L., Kumiski, D. H., Wallis, K. T., Stadt, H. A., Hutson, M. R., Platt, D. H., and Kirby, M. L. (2001). Conotruncal myocardium arises from a secondary heart field, Development 128, 3179-88.
64. Weissman, I. L. (2000). Translating stem and progenitor cell biology to the clinic: barriers and opportunities. Science 287, 1442-1446.
65. Wilkinson, D. G., ed. (1999). In Situ Hybridization: A Practical Approach, Second edition edn (Oxford University Press).
66. Winnier, G., Blessing, M., Labosky, P. A., and Hogan, B. L. (1995). Bone morphogenetic protein-4 is required for mesoderm formation and patterning in the mouse, Genes and Development 9, 2105-16.
67. Yuan, S., and Schoenwolf, G. C. (2000). Islet-1 marks the early heart rudiments and is asymmetrically expressed during early rotation of the foregut in the chick embryo, Anat Rec 260, 204-7.
68. Yutzey, K. E., and Kirby, M. L. (2002). Wherefore heart thou? Embryonic origins of cardiogenic mesoderm, Dev Dyn 223, 307-20.
69. Zhang, H., and Bradley, A. (1996). Mice deficient for BMP2 are nonviable and have defects in amnion/chorion and cardiac development, Development 122, 2977-86.

What is claimed is:

1. An in vitro method of culturing and expanding a cell population of undifferentiated mammalian cardiac progenitor cells substantially free of differentiated cells, comprising:
    culturing isolated undifferentiated mammalian progenitor cells that express Islet1 on a feeder layer of species-specific cardiac fibroblasts or conditioned medium from cardiac fibroblasts, thereby culturing and expanding a cell population of undifferentiated mammalian cardiac progenitor cells substantially free of differentiated cells.

2. The method of claim 1, wherein the undifferentiated progenitor cells are derived from mammalian non-myocyte cells.

3. The method of claim 2, wherein the mammalian non-myocyte cells are rat, mouse or human cells.

4. The method of claim 1, wherein the mammalian undifferentiated progenitor cells are derived from mammalian adult progenitor cells.

5. The method of claim 4, wherein the mammalian adult progenitor cells are derived from cardiac tissue of a rat, mouse or human.

6. An in vitro method of culturing and expanding a cell population of undifferentiated mammalian cardiac progenitor cells substantially free of differentiated cells, comprising:
    culturing isolated undifferentiated mammalian progenitor cells that express Islet1 and Nkx2.5 on a feeder layer of species-specific cardiac fibroblasts or conditioned medium from cardiac fibroblasts, thereby culturing and expanding a cell population of undifferentiated mammalian cardiac progenitor cells substantially free of differentiated cells.

7. The method of claim 6, wherein the mammalian undifferentiated progenitor cells are derived from mammalian non-myocyte cells.

8. The method of claim 7, wherein the mammalian non-myocyte cells are rat, mouse or human cells.

9. An in vitro method of culturing and expanding a cell population of undifferentiated mammalian cardiac adult stem cells substantially free of differentiated cells, comprising:
    culturing said isolated undifferentiated mammalian adult stem cells that express Islet1 on a feeder layer of species-specific cardiac fibroblasts or conditioned medium from cardiac fibroblasts, thereby culturing and expanding a cell population of undifferentiated mammalian cardiac adult stem cells.

10. The method of claim 9, wherein the undifferentiated mammalian adult stem cells are derived from mammalian non-myocyte cells.

11. The method of claim 10, wherein the mammalian non-myocyte cells are rat, mouse or human cells.

12. The method of claim 9, wherein the mammalian adult stem cells are postnatal stem cells.

13. The method of claim 9, wherein the mammalian adult stem cells are multipotent stem cells.

14. The method of claim 9, wherein the mammalian adult stem cells are mesenchymal stem cells.

15. The method of claim 9, wherein the mammalian adult stem cells further express Nkx2.5.

* * * * *